(12) United States Patent
Carney et al.

(10) Patent No.: US 9,933,402 B2
(45) Date of Patent: Apr. 3, 2018

(54) METHOD AND SYSTEM FOR DETERMINING THE LOCATION OF A FECAL INSULT

(71) Applicant: SCA Hygiene Products AB, Göteborg (SE)

(72) Inventors: Joshua Carney, Göteborg (SE); Henrik Carlén, Västra Frölunda (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/653,887

(22) PCT Filed: Dec. 21, 2012

(86) PCT No.: PCT/SE2012/051489
§ 371 (c)(1),
(2) Date: Jun. 19, 2015

(87) PCT Pub. No.: WO2014/098691
PCT Pub. Date: Jun. 26, 2014

(65) Prior Publication Data
US 2015/0301004 A1 Oct. 22, 2015

(51) Int. Cl.
*G01N 33/497* (2006.01)
*G01N 33/00* (2006.01)
(Continued)

(52) U.S. Cl.
CPC ........... *G01N 33/005* (2013.01); *A61F 13/84* (2013.01); *G01N 33/0047* (2013.01);
(Continued)

(58) Field of Classification Search
CPC ........... G08B 21/12; A61F 2013/8491; G01N 33/0075
See application file for complete search history.

(56) References Cited

U.S. PATENT DOCUMENTS

| 5,709,222 A | 1/1998 | Davallou |
| 7,642,396 B2 | 1/2010 | Ales, III et al. |

(Continued)

FOREIGN PATENT DOCUMENTS

| CN | 101668499 A | 3/2010 |
| EP | 2518479 A1 | 10/2012 |

(Continued)

OTHER PUBLICATIONS

L.M. Ang et al., "Wireless Intelligent Incontinence Management System using Smart Diapers," Electrical Engineering/Electronics, Computer, Telecommunications and Information Technology, Proceedings of ECTI-CON, 2008, pp. 69-72, vol. 1.

(Continued)

*Primary Examiner* — Daniel Larkin
*Assistant Examiner* — Alex Devito
(74) *Attorney, Agent, or Firm* — Drinker Biddle & Reath LLP

(57) ABSTRACT

A method for determining the location of a fecal insult, includes: detecting the concentration of at least one gas indicative of feces at a plurality of locations in a defined space; and determining whether said concentration of said gas exceeds a predetermined first threshold value. The method includes: detecting the concentration of hydrogen gas at each of said locations; detecting the concentration of at least one further gas component being indicative of feces in said space; and determining that a fecal insult has occurred in a location where said detected concentration of hydrogen gas exceeds said first threshold value, provided that the detected concentration of said further gas component also exceeds a predetermined second threshold value in said location.

10 Claims, 6 Drawing Sheets

(51) Int. Cl.
  *G08B 21/12* (2006.01)
  *A61F 13/84* (2006.01)
  *A61F 13/42* (2006.01)
  *A61F 13/15* (2006.01)

(52) U.S. Cl.
  CPC ......... *G01N 33/0075* (2013.01); *G08B 21/12* (2013.01); *A61F 13/42* (2013.01); *A61F 2013/15138* (2013.01); *A61F 2013/8491* (2013.01)

(56) References Cited

U.S. PATENT DOCUMENTS

| | | |
|---|---|---|
| 2004/0147888 A1 | 7/2004 | Huang et al. |
| 2004/0173006 A1 | 9/2004 | McCoy et al. |
| 2005/0099294 A1 | 5/2005 | Bogner et al. |
| 2007/0142799 A1* | 6/2007 | Ales ............... A61F 13/42 604/361 |
| 2007/0156456 A1* | 7/2007 | McGillin ............ G06F 19/327 705/2 |
| 2010/0072271 A1 | 3/2010 | Thorstensson |
| 2011/0095884 A1 | 4/2011 | Xu et al. |
| 2012/0072271 A1 | 3/2012 | Dessert et al. |
| 2012/0119915 A1 | 5/2012 | Clement et al. |
| 2012/0206265 A1 | 8/2012 | Solazzo |
| 2012/0268278 A1 | 10/2012 | Lewis et al. |
| 2012/0310192 A1 | 12/2012 | Suzuki et al. |
| 2015/0330958 A1 | 11/2015 | Carney et al. |

FOREIGN PATENT DOCUMENTS

| | | |
|---|---|---|
| JP | 2001-314433 | 11/2001 |
| JP | 2002-107361 | 4/2002 |
| JP | 2003-270242 | 9/2003 |
| JP | 2005 315836 A | 11/2005 |
| JP | 2006-206876 | 8/2006 |
| JP | 2007-167264 A | 7/2007 |
| JP | 2009-521259 | 6/2009 |
| JP | 2010-075463 | 4/2010 |
| JP | 3168620 U | 6/2011 |
| JP | 2011-130924 | 7/2011 |
| KR | 2009-0006641 U | 7/2009 |
| KR | 2009 0119157 A | 11/2009 |
| WO | WO-96/14813 A1 | 5/1996 |
| WO | WO-02/49561 A1 | 6/2002 |
| WO | WO 2005/039656 A1 | 5/2005 |
| WO | WO-2006/119523 A1 | 11/2006 |
| WO | WO 2007/073428 A1 | 6/2007 |
| WO | WO 2011/054045 A1 | 5/2011 |
| WO | WO 2011/078325 A1 | 6/2011 |
| WO | WO-2012/126507 A1 | 9/2012 |
| WO | WO 2013/061181 A1 | 5/2013 |

OTHER PUBLICATIONS

English-language translation of a Japanese Office Action dated Aug. 28, 2016 issued in corresponding Japanese patent application No. 2015-549309 (5 pages).

Extended European search report dated Aug. 3, 2016 issued in related European patent application No. EP 12890394.5 (6 pages).

English-language translation of a Japanese Office Action dated Jun. 13, 2016 issued in related Japanese patent application No. 2015-549308 (3 pages).

Supplementary European Search Report dated Jun. 23, 2016 issued in corresponding European patent application No. EP 12 89 0310 (2 pages).

Office Action dated Feb. 17, 2017 in Russian Patent Application No. 2015129717/14 (5 pages) with an English translation (3 pages).

Office Action dated Jun. 3, 2017 in Colombia Patent Application No. 15168122 (12 pages) with a partial English translation (7 pages).

* cited by examiner

METHOD AND SYSTEM FOR DETERMINING THE LOCATION OF A FECAL INSULT

CROSS-REFERENCE TO PRIOR APPLICATION

This application is a § 371 National Stage Application of PCT International Application No. PCT/SE2012/051489 filed Dec. 21, 2012, which is incorporated herein in its entirety.

TECHNICAL FIELD

The present disclosure relates to a method for determining the location of a fecal insult, including: detecting the concentration of at least one gas indicative of feces at a plurality of locations in a defined space; and determining whether said concentration of said gas exceeds a predetermined first threshold value.

The disclosure also relates to a system for determining the location of a fecal insult, including: a first gas sensor for detecting the concentration of at least one gas indicative of feces at a plurality of locations in a defined space; and a receiver unit for determining whether said concentration of said gas exceeds a predetermined first threshold value.

BACKGROUND ART

Lifestyle choices, life-prolonging medicines and a general rise in living standard are some of the things that have led to an aging population. Many elderly people are hospitalized in their late years and bound to their beds by medical reasons. For this reason, the aging population has led to an increase in stays at care homes. One issue of care homes is the care of patients that suffer from urinal and/or fecal incontinence.

If a patient cannot have his/her sanitary article changed relatively quickly after an insult of feces or urine has occurred, the patient may face problems with uncomfort, and even degeneration of skin health, such as rashes and pressure ulcers. Further, it is unpleasant for a patient who suffers from incontinence not to be able to indicate if an insult has occurred, which is sometimes the case for patients suffering from e.g. dementia or incapacitation.

On the other hand, if the sanitary article is changed too often-which may be the result of routines in a care home, stating for example that sanitary articles should be changed every four hours (independently if whether there have occurred insults or not)-this may lead to an unnecessarily high consumption of sanitary articles. This is of course a disadvantage as regards cost.

Commonly, the routine of changing sanitary articles in a care home or hospital, for example, depend on the time schedule of the nurses' rounds and thus patients may have to wear a soiled sanitary article for a long time. During these rounds, the nurses rely on visual inspection and odor to decide if an absorbent article needs changing.

Also, it is common that several patients share one room, so even if a nurse detects that an insult has occurred in the room by the odor of feces, the nurse has to determine which one of the patients that needs changing. This scenario is also possible in a children's hospital or in natal care where the children wear diapers.

The pungent odors associated with feces are due to a complex mixture of compounds produced by bacterial action which result in odorous gases emitted, and detection of fecal insults may be made using sensors based on the detection of these gases. Such gas sensors are previously known.

Gases with strong odor emitted from feces include gases such as indole, skatole and mercaptans as well as hydrogen sulfide and ammonia. In particular, heavy organic compounds such as mercaptans (methyl sulfides) and hydrogen sulfide may spread widely as well and linger in a room after a fecal insult occurred. Hydrogen gas is also associated with feces, but is a volatile gas and hence does not travel far or linger as long as the heavier gases.

Gases specific for feces and urine may be used to detect the occurrence of a fecal insult. The patent U.S. Pat. No. 5,709,222 discloses a body waste detector that includes a gas sensor adapted to detect the presence of at least one gas associated with urine and at least one gas associated with feces over a predetermined time interval. Thereafter, the detector indicates the presence of waste. The system is used for detecting the local presence of body waste of one person. Therefore, each possible source of body waste must be provided with a detector, and each detector must be inspected in order to determine if and where feces are present.

Based on the issues set forth above, there is a need for improved systems and methods in order to detect the occurrence of a fecal insult as well as determine the location of the insult in an accurate and reliable manner.

SUMMARY

It is desired to provide an improved method for determining the location of a fecal insult in a defined space with high accuracy and reliability, as well as to provide a system for the same. The method and system described herein achieve these desired improvements and may for example be used in hospitals and care homes for detecting the occurrence of a fecal incontinence insult as well as the location of the fecal insult. They may also be used in public washrooms for identifying the location of a fecal contamination e.g. an insult.

The present disclosure provides a method for determining the location of a fecal insult, including: detecting the concentration of at least one gas indicative of feces at a plurality of locations in a defined space; and determining whether said concentration of said gas exceeds a predetermined first threshold value. The method further includes detecting the concentration of hydrogen gas at each of said locations; detecting the concentration of at least one further gas component being indicative of feces in said space; and determining that a fecal insult has occurred in a location where said detected concentration of hydrogen gas exceeds said first threshold value, provided that the detected concentration of said further gas component also exceeds a predetermined second threshold value in said location.

Accordingly, the presence of feces is confirmed by the detection of two gases which are different from each other, both gases being indicative of feces. Hence, the method is reliable and accurate. Further, the location of the fecal insult is determined as the location in which the concentration of the detected hydrogen gas exceeds a first threshold value. Hydrogen gas is volatile and does not spread widely in a defined space. For this reason, the location corresponding to the detected hydrogen gas also corresponds to the location of the fecal insult. The detection of at least one further gas component being indicative of feces confirms the presence of a fecal insult, i.e. that the detected hydrogen gas is not due to another hydrogen gas source than the fecal insult.

In one embodiment, the detected concentration of the further gas component exceeds the second threshold value in the location where the detected concentration of hydrogen gas exceeds the first threshold value.

The detected concentration of the further gas component may exceed the second threshold value in a location different from the location where the detected concentration of hydrogen gas exceeds said first threshold value. The detection of the further gas component thus confirms the presence of a fecal insult irrespective of which of the plurality of two locations hydrogen gas concentration is detected in. As a result, only one location is normally needed for detecting the further gas component. This is due to the distribution properties of the further gas component.

In certain embodiments, if detecting the concentration of the further gas component is done in a location different from the location where the detected concentration of hydrogen gas exceeds the first threshold value, it is detected at equal distance of the locations where hydrogen gas component is detected. Hence, detecting a further gas component may be performed in one location in the defined space whereas detecting of hydrogen gas is performed in at least two locations. Thus, less detection locations are needed, and the detection of a further gas component may be used to confirm several fecal insults located at locations of hydrogen gas detection.

The further gas sensor may be arranged within the area of distribution of the further gas originating from feces but out of the distribution area of hydrogen gas originating from feces.

In certain embodiments, the further gas component is an organic compound and/or hydrogen sulphide, and thus spreads and lingers in a defined space following a fecal insult. It may therefore be used to confirm the presence of a fecal insult even if it is detected at a location in the defined space different from the location where hydrogen gas exceeding a first threshold is detected. As an effect, the hydrogen gas component may be detected in several locations in the defined space in order to determine the location of the insult, but the location is determined by the location of where the hydrogen component concentration exceeds a first threshold value. The presence of a further gas component, e.g. hydrogen sulfide, is used as a confirmation that the source of hydrogen component is indeed a fecal insult. As a result, the method is reliable in terms of detecting a true fecal insult (distinguishing a fecal insult from other possible gas sources) as well as determining the location in the defined space that the insult occurred.

In order to further increase the reliability of the method, the method may further include determining that feces is present where the detected concentration of hydrogen gas and/or the detected concentration of the further gas component exceed the first and second threshold values, respectively, during a predetermined period of time. When the gas components are detected over a predetermined period of time, it is possible to rule out that the source of the gas components is an intestinal gas release, e.g. passing wind, or other sources. Gas from passing wind does not linger in the defined space for as long as the gas components from a fecal insult, and may thus be distinguishable from each other.

In one aspect, the method includes assigning a weight value for each of the concentration of hydrogen gas and a further gas component before determining that feces is present in a location. Thereby, the presence of hydrogen gas components may be given more importance than the further gas component.

According to one aspect, the locations in the defined space of detecting the concentration of hydrogen gas are at a predetermined distance from each other and the predetermined distance is longer than the radial distance that hydrogen gas may travel from its source of origin before the concentration of hydrogen gas component is no longer detectable. By arranging the locations of detecting hydrogen gas components at such a distance, there is no risk of one location being reached by hydrogen gas originating from another source, and thus being detected at two different locations. The distance thereby guarantees that the method of locating the fecal insult is accurate and reliable.

The method may also include the step of registering the location of presence of feces in a receiving unit. Personnel may then advantageously identify the location of the fecal insult by monitoring the receiving unit instead of performing a manual inspection. This is of great value to the personnel in e.g. a care home, hospital or cleaning staff of public washrooms as time and labor can be saved. The receiving unit may further be arranged to communicate with a central unit or a mobile unit such as a mobile phone or a computer tablet. Thereby, the personnel may receive information regarding the location of fecal insults directly to a mobile phone which facilitates planning of the round, working day, logistics etc.

It can be advantageous when the defined space is a hospital room or a public washroom but the method described herein may also be used in other defined spaces in which it is an advantage to be able to determine the locations of fecal insults.

The disclosure also concerns a system for determining the location of a fecal insult, including: a first gas sensor for detecting the concentration of at least one gas indicative of feces at a plurality of locations in a defined space; and a receiver unit for determining whether said concentration of said gas exceeds a predetermined first threshold value. The system is arranged so that said first gas sensor is configured for detecting the concentration of hydrogen gas at each of said locations; that it includes at least one further gas sensor detecting the concentration of at least one further gas component being indicative of feces in said space; said receiver unit being arranged for determining that a fecal insult has occurred in a location where said detected concentration of hydrogen gas exceeds said first threshold value, provided that the detected concentration of said further gas component also exceeds a predetermined second threshold value in said location.

The receiver unit is arranged for providing an indication of the location of the presence of feces based on information from the sensors. The locations of fecal insults are thereby available to users of the receiving unit. Such a system is advantageous for example for staff in a hospital receiving information regarding which patient in a hospital room has had an fecal insult.

The further sensor unit may include at least two gas sensors arranged to detect at least two further gas components, other than hydrogen, being indicative of feces. Example of suitable other gas components include hydrogen sulfide and heavy organic compounds that are not volatile and thus spread and linger in the defined space. By detecting two gases indicative of feces, other than hydrogen gas, the system will be more reliable.

The receiving unit may include an indicator for providing visual or aural information as to the location where feces have been detected, such that the information is readily and easily conveyed to the user. The receiving unit may be arranged in the defined space, but may also be arranged outside the space. The system may further include a remote server unit connectable to the receiving unit and for storing information from the gas sensors. Thereby, statistics concerning fecal insults may be saved. The compiled information may also be used for planning staffing, rounds, logistics etc. It is also plausible that the remote server unit is connected to a mobile phone or computer tablet. Potentially, the mobile phone is provided with an alarm system which provides a signal when a fecal insult has occurred. The receiving unit may also be a mobile phone or tablet computer.

In particular embodiments, the at least two sensor units arranged to detect the concentration of hydrogen gas are arranged at a predetermined distance from each other and the predetermined distance is longer than the radial distance that hydrogen gas may travel from its source of origin before said concentration of hydrogen is no longer detectable. Thereby there is no risk of a hydrogen gas sensor in a first location to provide a positive reading based on hydrogen gas present at a second location.

It is also possible to use several further sensor units each arranged in association with each hydrogen sensor.

BRIEF DESCRIPTION OF THE DRAWINGS

Embodiments of the invention will be described more fully hereinafter with reference to the accompanying drawings. The invention may, however, be embodied in many different forms and should not be construed as limited to the examples set forth herein, wherein.

DETAILED DESCRIPTION OF PARTICULAR EMBODIMENTS

Figure 1:
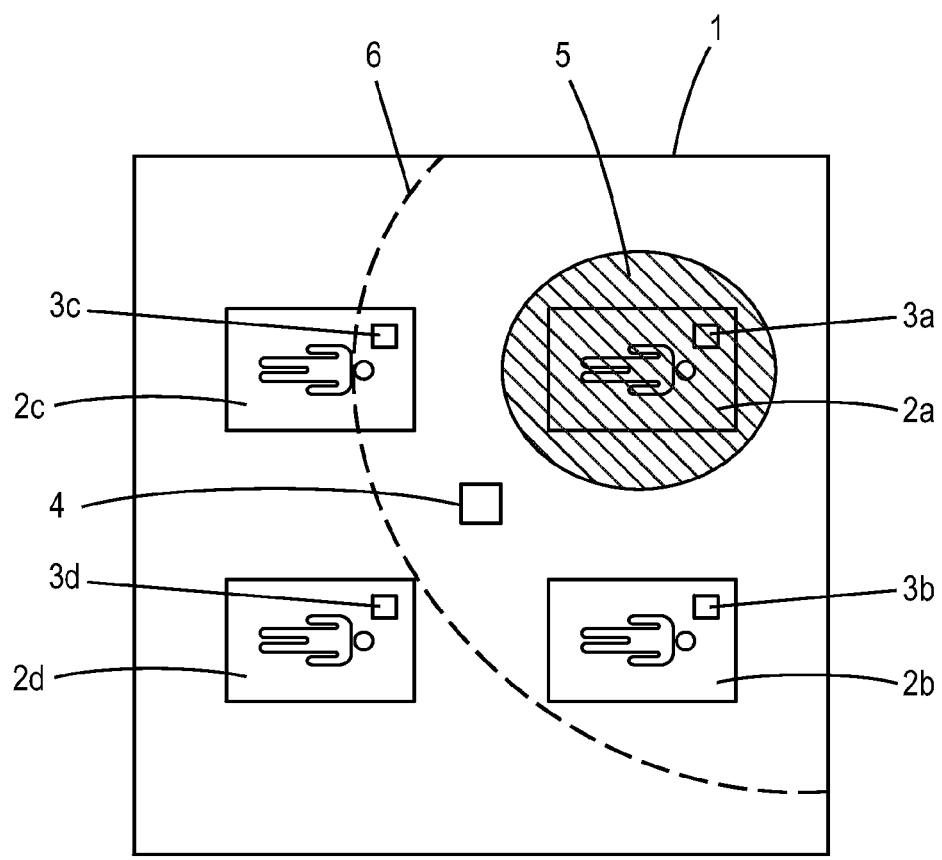
FIG. 1 shows a schematic view of a hospital room provided with a system according to an embodiment of the invention.

FIG. 1 shows a view from above of a defined space 1, exemplified by a hospital room, in which four beds 2a, 2b, 2c, 2d are arranged. The beds 2a, 2b, 2c, 2d are for the use of bed confined patients, who in this embodiment suffer from urinal and/or fecal incontinence and therefore wear sanitary articles, such as absorbent incontinence pads or diapers. Further, according to the embodiment, it can be expected that the patients cannot themselves change their sanitary article and possibly also cannot communicate the need to change the sanitary article following a urinal or fecal insult.

A first type of gas sensor 3a, 3b, 3c, 3d, suitably including a gas sensor which may detect the presence of at least one gas which is indicative of feces, is arranged in, or in the vicinity of, each bed 2a, 2b, 2c, 2d. In accordance with the embodiment, the gas sensors 3a, 3b, 3c, 3d are sensitive to hydrogen gas. This means that the gas sensors 3a, 3b, 3c, 3d can be used for detecting the concentration of a hydrogen gas component following an occurrence of a fecal insult by any of the patients in the respective bed 2a, 2b, 2c, 2d.

In the embodiment, a fecal insult has occurred in bed 2a. A further sensor unit 4, being able to detect gas components indicative of feces other than hydrogen e.g. hydrogen sulfide and/or heavy organic compounds, is arranged in a location generally in the centre of the room 1.

In the following, the principles exemplified by embodiments of the invention will be described with the assumption that a fecal insult has occurred in the bed indicated with reference numeral 2a. As a result of the fecal insult in the bed 2a, gas including a variety of components from the feces is emitted in the hospital room 1. Hydrogen gas is instantly spreading in a distribution area 5 around the bed 2a. Due to the volatility of hydrogen gas, the distribution area 5 of hydrogen gas is relatively small. Also, other gas components indicative of the presence of feces, such as heavier organic compounds and hydrogen sulfide, are also spreading in the room 1. However, due to the fact that the heavy organic compounds and hydrogen sulfide are heavier, they have a tendency to spread out more slowly and in a more widespread distribution area, which is indicated by reference numeral 6 in FIG. 1. Consequently the distribution area 5 of hydrogen gas is substantially smaller than the distribution area 6 of heavy organic compounds and hydrogen sulfide.

The two types of gases-i.e. hydrogen gas on the one hand and heavy organic compounds and hydrogen sulfide on the other hand-spread out in different ways in the event of a fecal insult. According to embodiments of the method, the fecal insult which has occurred in the bed 2a will give rise to hydrogen gas which is detected by the hydrogen gas sensor 3a arranged at the bed 2a in the hospital room 1. If the detected hydrogen gas concentration is above a predetermined threshold value for hydrogen gas, this is determined to correspond to a fecal insult. In other words, if the hydrogen gas concentration detected by means of the gas sensor 3a if higher than a predetermined threshold level which corresponds to the expected level resulting from a fecal insult, the gas sensor 3a interprets this as a fecal insult. In order to obtain a more reliable and accurate result, the second gas sensor 4 for heavy organic compounds and hydrogen sulfide is also used to detect a further gas concentration.

Due to the fact that heavy organic compounds and hydrogen sulfide spread out more widely into the area 6, they can be detected by means of the second gas sensor 4 which is positioned generally in the centre of the room 1. If the gas concentration detected by means of the second gas sensor 4 is higher than a predetermined threshold level which corresponds to the expected level resulting from a fecal insult, the second gas sensor 4 interprets this as a fecal insult.

In one aspect, the method includes assigning a weight value for each of the concentration values of hydrogen gas and a further gas component before determining that feces is present in a location. Thereby, the presence of hydrogen gas components may be given more importance than the further gas component. This also means that the combined readings from the first gas sensor 3a and the second gas sensor 4 can be used to obtain a reliable and accurate indication as to the location of the fecal insult, i.e. the bed 2a.

The presence of a further gas component, e.g. hydrogen sulfide, is consequently used as a confirmation that the source of hydrogen gas component is indeed a fecal insult.

According to the embodiment, the further gas sensor 4 is arranged at equal distance to the locations where hydrogen gas can be expected to be detected, i.e. the location of the hydrogen gas sensors $3a$, $3b$, $3c$, $3d$ which are arranged at each bed $2a$, $2b$, $2c$, $2d$. Thereby, further gas sensor 4 is arranged within the area of distribution 6 of further gas originating from feces at each bed $2a$, $2b$, $2c$, $2d$, but out of the distribution area 5 of hydrogen gas originating from feces at each bed $2a$, $2b$, $2c$, $2d$.

Figure 2:
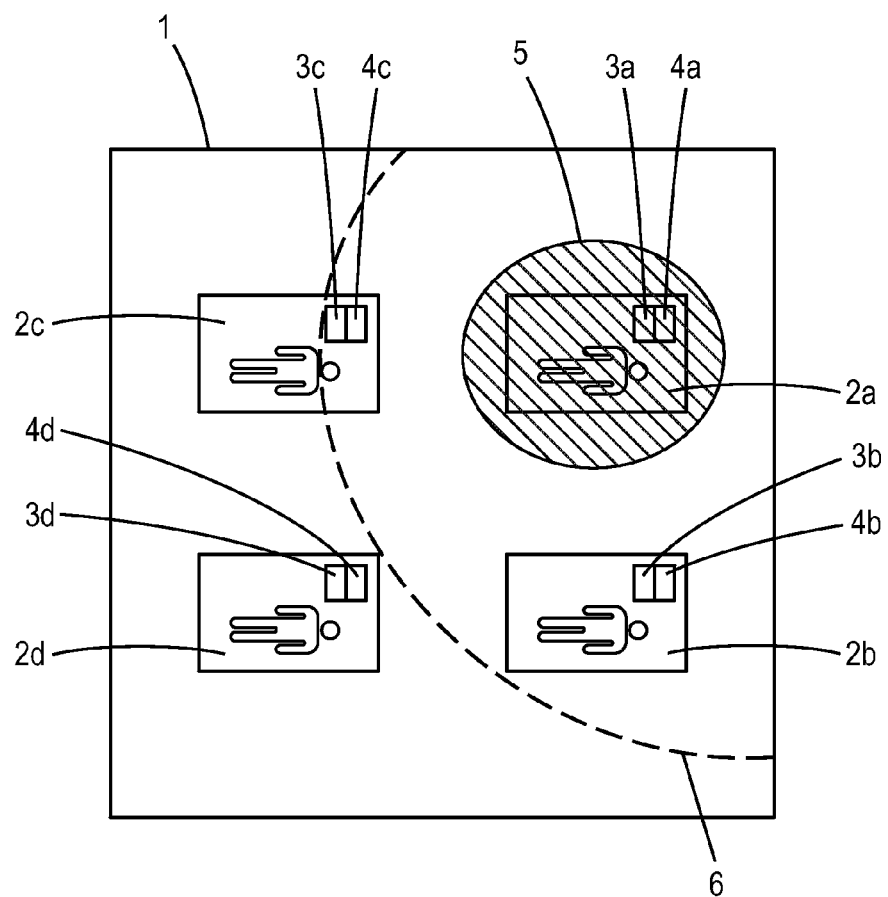
FIG. 2 shows a schematic view of a hospital room provided with a system according to an alternative embodiment of the invention.

FIG. 2 is a view of an embodiment which generally corresponds to FIG. 1 and which includes a first type of gas sensor $3a$, $3b$, $3c$, $3d$, suitably including a gas sensor which may detect the presence of at least one gas which is indicative of feces, is arranged in, or in the vicinity of, each bed $2a$, $2b$, $2c$, $2d$. In accordance with the embodiment, the gas sensors $3a$, $3b$, $3c$, $3d$ are sensitive to hydrogen gas. Furthermore, the embodiment shows a second type of gas sensor $4a$, $4b$, $4c$, $4d$, being able to detect gas components indicative of feces other than hydrogen e.g. hydrogen sulfide and/heavy organic compounds.

As shown in FIG. 2, a gas sensor unit is formed at each bed $2a$, $2b$, $2c$, $2d$, i.e. consisting of a first gas sensor and second gas sensor combined together. Suitably, with reference to the first bed $2a$, this is implemented in the form of an integrated gas sensor unit comprising one hydrogen sensor $3a$ and one further sensor $4a$ for heavy organic compounds and/or hydrogen sulfide. Similar arrangements are implemented in, or in close vicinity of, the other beds $2b$, $2c$, $2d$.

It should be mentioned that in many cases, only one location is normally needed for detecting the further gas component. This is due to the distribution properties of the further gas component. However, FIG. 2 shows a possible variation of the embodiment shown in FIG. 1.

Consequently, the embodiment shown in FIG. 2 shows four distributed sensors $4a$, $4b$, $4c$, $4d$ instead of one single sensor positioned generally in the centre of the room 1, as shown in FIG. 1.

If a fecal insult occurs in the first bed $2a$, hydrogen gas will spread out in a distribution area 5, which is relatively small due to the volatile nature of hydrogen gas. Also, as explained above, heavy organic compounds and hydrogen sulfide are also spread out, but over a larger area 6.

If the detected hydrogen gas concentration, as detected by the first gas sensor $3a$, is above a predetermined threshold value for hydrogen gas, this is determined to correspond to a fecal insult. Also, if the detected gas concentration by means of the second gas sensor $4a$ (at the first bed $2a$) is higher than a predetermined threshold level which corresponds to the expected level resulting from a fecal insult, the second gas sensor $4a$ interprets this as a fecal insult. The combined reading from both sensor stating that the conditions for determining that a fecal insult has occurred is consequently a reliable and accurate solution.

The hydrogen gas in the room 1 can also be detected by the other hydrogen gas sensors $3b$, $3c$, $3d$, but the concentrations are below the first threshold value. The further gas components, i.e. heavy organic compounds and hydrogen sulfide, can be detected by the second sensor $4a$. It can be noted that in the situation shown in FIG. 2, the area 6 over which the organic compounds and hydrogen sulfide are spread also covers the sensor units at the second bed $2b$ and the second $2c$. This means that the sensors for organic compounds and hydrogen sulfide at the second bed $2b$ and third bed $2c$, i.e. the sensors indicated by reference numerals $4b$ and $4c$, respectively, may detect a gas concentration which may exceed the above-mentioned threshold value. However, the hydrogen gas has a relatively small distribution area 5 and organic compounds and hydrogen sulfide has a relatively large distribution area 6, which in this case means that if the first sensor $3a$ at the first bed $2a$ and the second sensor $4a$ at the first bed $2a$ both indicate that the gas concentrations is above the relevant threshold levels, an indication of a fecal insult at the first bed $2a$ can be issued.

In particular embodiments, the distance between each one of the first sensors $3a$, $3b$, $3c$, $3d$ is greater than the expected distance over which the volatile hydrogen gas may spread.

Figure 3:
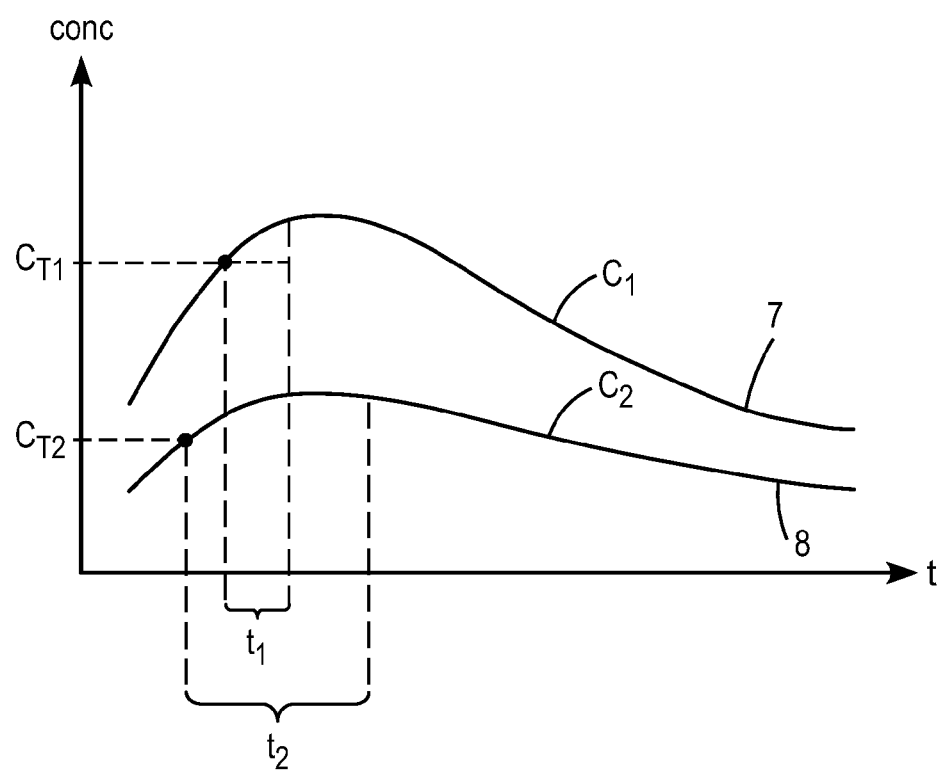
FIG. 3 is a diagram explaining principles exemplified by embodiments of the invention.

FIG. 3 is a diagram showing the gas concentrations as measured by the first gas sensor $3a$ and the second gas sensor 4 shown in FIG. 1 (alternatively the second gas sensor $4a$ shown in FIG. 2). A first curve 7 indicates the concentration $c_1$ of hydrogen gas as detected by the first sensor $3a$ a result of a fecal insult, whereas a second curve 8 indicates the concentration $c_2$ of heavy compounds and hydrogen sulfide, as detected by the second sensor 4 (alternatively $4a$).

If the hydrogen gas concentration $c_1$ exceeds a predetermined threshold value $c_{T1}$ at least a predetermined first time period $t_1$, this is an indication of a fecal insult. Also, if the concentration $c_2$ of organic compounds and hydrogen sulfide exceeds a predetermined second threshold value $c_{T2}$ during a second time period $t_2$, this is regarded as a fecal insult. A fecal insult is deemed to have occurred if said detected concentration $c_1$ of hydrogen gas exceeds said first threshold value $c_{T1}$, provided that the detected concentration $c_2$ of said further gas component also exceeds a predetermined second threshold value $c_{T2}$ in said location $2a$.

When the gas components are detected over a predetermined period of time, it is possible to rule out that the source of the gas components is an intestinal gas release, e.g. passing wind, or other sources. Gas from passing wind does not linger in the defined space for as long as the gas components from a fecal insult, and may thus be distinguishable from each other.

In another example, not shown, a fecal insult has occurred in beds $2a$ and $2b$. A concentration of hydrogen gas above a first threshold is subsequently detected by the sensors $3a$, $3b$ arranged at the two beds $2a$, $2b$. The concentrations of hydrogen gas detected by the remaining sensors $3c$, $3d$ are below the first threshold value. The concentration of gas detected by the further sensor 4 is above a second threshold value and thus confirms the presence of feces in the hospital room 1. Thereby, feces is determined to the two locations where the detected concentration of hydrogen gas exceeds the first threshold value, i.e. fecal insults are located to be present in beds $2a$ and bed $2b$ respectively.

Figure 4:
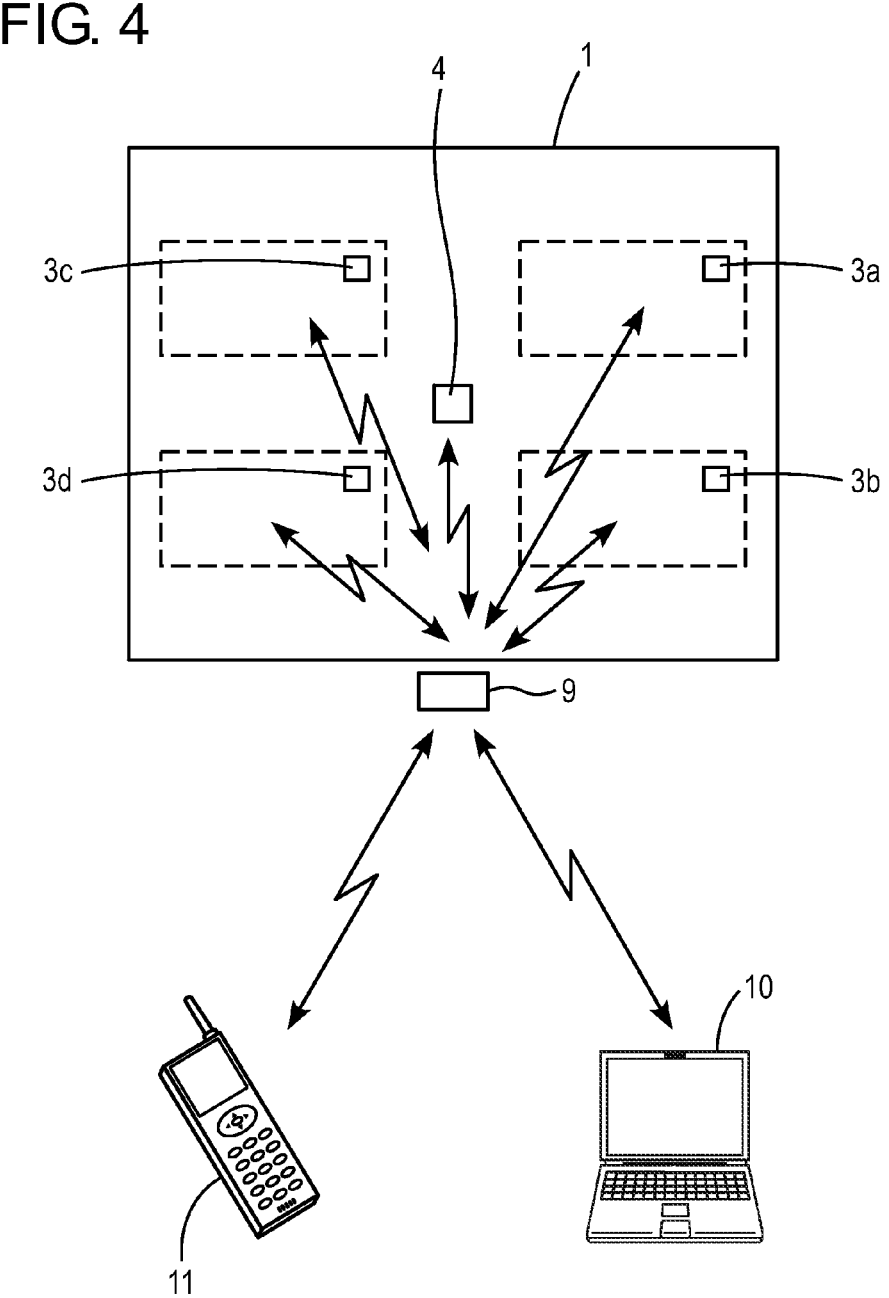
FIG. 4 shows principles exemplified by embodiments of the invention with regard to a network of data communication.

FIG. 4 shows the principles of a system according to an embodiment of the invention. The system shown in FIG. 4 corresponds to FIG. 1 but shows merely the first gas sensors $3a$, $3b$, $3c$, $3d$ and the second sensor 4. All these sensors $3a$, $3b$, $3c$, $3d$, 4 are arranged to communicate with a receiver unit 9 which can be a data communication unit which is arranged in the vicinity of the sensors $3a$, $3b$, $3c$, $3d$, 4. In particular embodiments, the connection between the sensors $3a$, $3b$, $3c$, $3d$, 4 and the receiver unit 9 is wireless, and can be based on suitable wireless technology such as Bluetooth or Zigbee. Such nearfield communication technologies are well-known to the skilled person, and for this reason they are not described in greater detail here.

The system is suitably implemented so that the sensors $3a$, $3b$, $3c$, $3d$, 4 transmit their measurements regarding the gas concentrations, as mentioned above, to the receiver unit 9. The receiver unit 9 is then configured for determining whether the gas concentrations for hydrogen gas, heavy organic compounds and hydrogen sulfide exceed their predetermined associated threshold values.

Furthermore, the receiving unit 9 may include an indicator for providing visual or aural information as to the location where the fecal insult has occurred, such that the information is readily and easily conveyed to the user. The receiving unit 9 may be arranged in the room 1, or outside the room 1. The system may further include a remote server unit 10 connectable to the receiving unit 9 and for storing information from the gas sensors 3a, 3b, 3c, 3d, 4. Thereby, statistics concerning fecal insults may be saved. The compiled information may also be used for planning staffing, rounds, logistics etc. It is also plausible that the remote server unit 10 or the receiver unit 9, or both, is connected to a mobile unit 11, such as a mobile phone or tablet computer. The user of the mobile units may then receive instant information from the sensors, e.g. the location of a fecal insult directly following the time of the insult. Also, the mobile unit 11 is provided with an alarm system which provides a signal when a fecal insult has occurred. The user of the mobile unit 10, e.g. a caregiver, may thus be notified that a fecal incident has occurred in a specific location (2a), and go there to change the sanitary article of the person in the bed 2a in question. The receiving unit 9 may also be a mobile phone or tablet computer.

Figure 5:
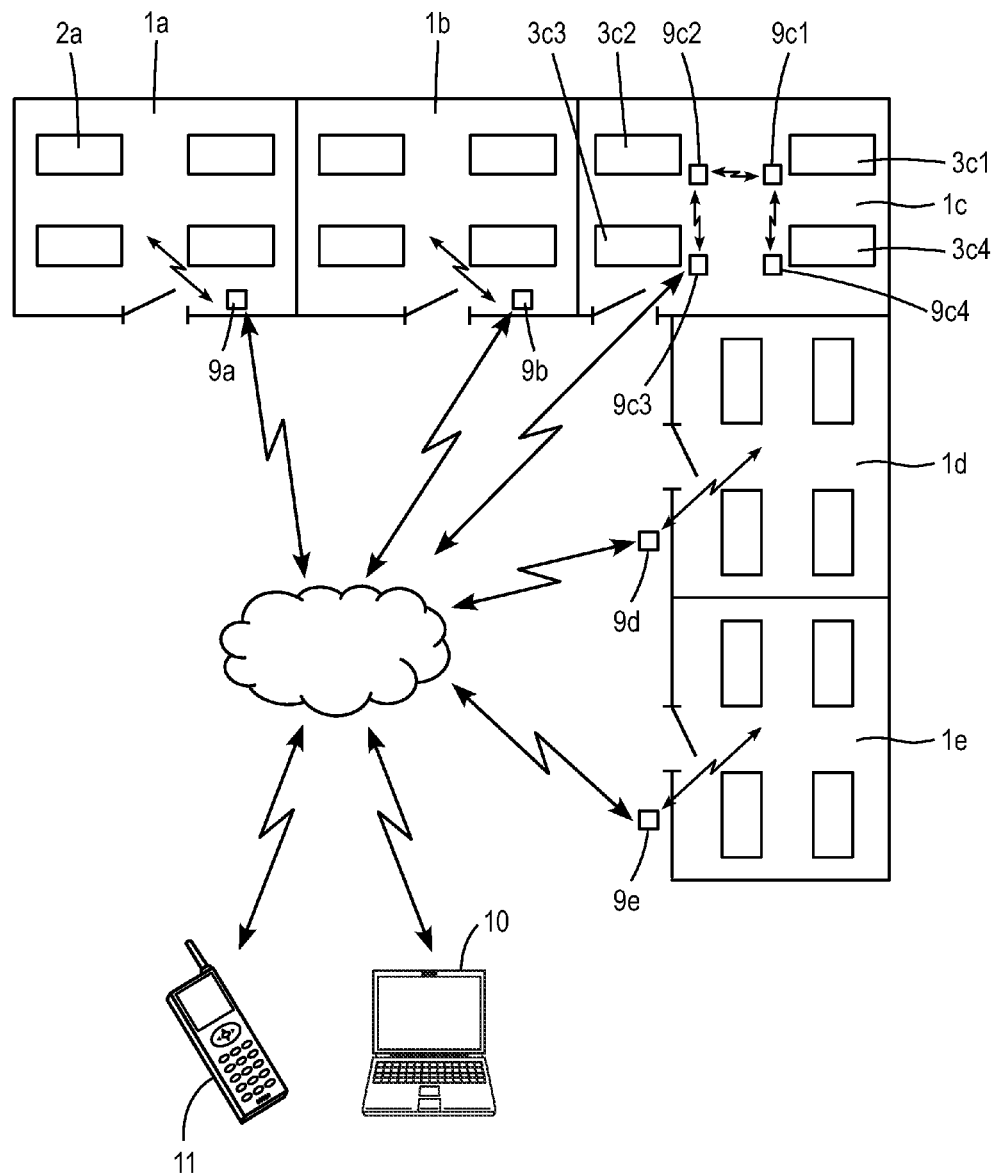
FIG. 5 shows a schematic view of a plurality of rooms being configured in accordance with an embodiment of the invention.

FIG. 5 shows a plurality of hospital rooms 1a, 1b, 1c, 1d, 1e and also indicates a larger network solution in which embodiments of the invention can be implemented. This means that each room 1a, 1b, 1c, 1d, 1e has a number of receiver units, or data collecting units, as will be described below. These receiver units communicate with a number of gas sensors (not shown in FIG. 5) in each room as described above.

In order to explain the principles of embodiments of the invention, FIG. 5 shows different types of arrangements for said receiver units. More precisely, the first room 1a has a receiver unit 9a which is positioned inside the room 1a and which communicates with sensors within said room 1a. The second room 1b has a similar receiver unit 9b which is also positioned inside said room 1b. Furthermore, the third room 1c has a number of receiver units 9c1, 9c2, 9c3, 9c4, which are positioned at each corresponding bed 3c1, 3c2, 3c3, 3c4 and which communicate with gas sensors arranged at each bed as explained above with reference to FIG. 1 or FIG. 2.

Furthermore, the fourth room 1d has a receiver unit 9d which is positioned outside said room 1d. Similarly, the fifth room 1e has a receiver unit 9e which is positioned outside said room 1e.

All receiver units 9 are suitably configured for collecting sensor data and for transmitting said sensor data to a remote server unit 10 which is arranged for storing information from all the gas sensors within the network. As mentioned above, the compiled information may be used for example for planning staffing and logistics. The remote server unit 10 or the receiver units 9, or both, are suitably connected to a mobile unit 11, such as a mobile phone or tablet computer.

According to an embodiment, the receiver units 9c1, 9c2, 9c3, 9c4 in the third room 1c are arranged as a "daisy chain", i.e. according to a scheme in which the data signals are transmitted in a sequence from a first receiver unit to a last one, in a ring or chain, wherein a last one of the receiver units (i.e. receiver unit 9c3 in FIG. 5) is configured to communicate with an external network and the remote server 10.

One benefit of using the system in hospital rooms is thus that a staff member managing the diaper changes of the patients in the hospital room does not have to perform manual inspection of patients, but receives accurate and reliable information concerning the location of fecal insults from a receiver unit. Manual labor may consequently be saved.

The principles of embodiments of the invention can be implemented in larger networks including different facilities, for example several hospitals or similar sites. In such case, a number of rooms or departments can be connected in a network, for example in the form of a wireless data communication network, in order to allow detection fecal insults and for transmitting related information to one or more remote, central servers. Such communication may allow, for example, planning of staff, care of patients and cleaning operations in an efficient and centralized manner.

Figure 6:
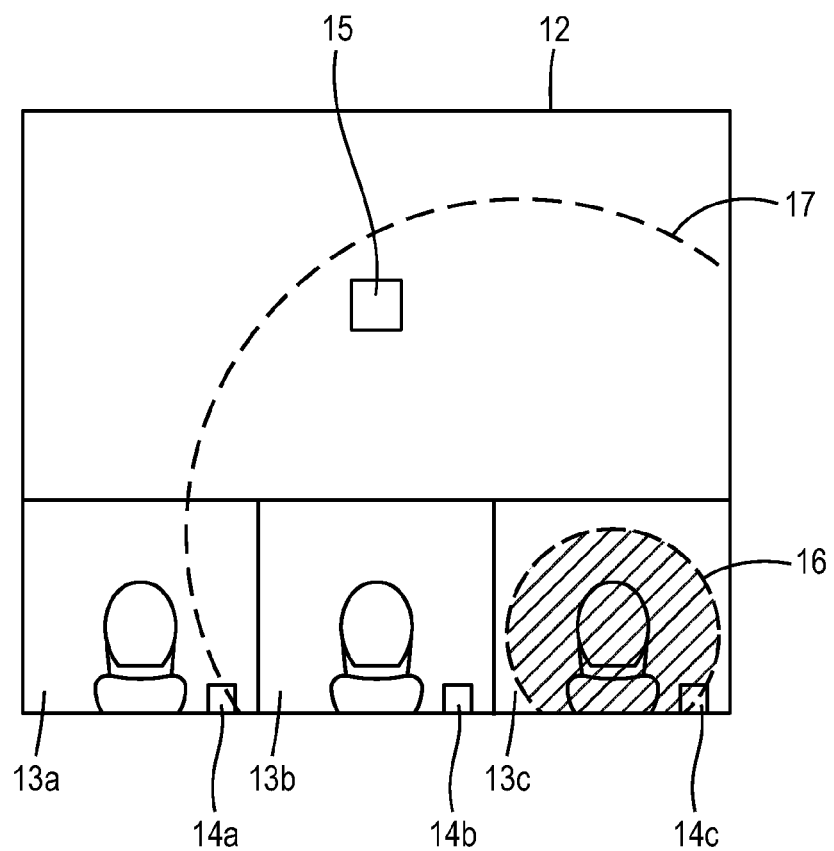
FIG. 6 shows a schematic view of a public washroom provided with a system according to an embodiment of the invention.

FIG. 6 shows another example of an embodiment of the present invention. In the example, the defined space 12 is represented by a public washroom including three cubicles 13a, 13b, 13c. Hydrogen gas sensors 14a, 14b, 14c are arranged at each cubicle 13a, 13b, 13c and a further gas sensor 15 is arranged at a distance from each hydrogen sensor 14a, 14b, 14c. A fecal insult may be determined to the location of the hydrogen gas sensor 14a, 14b, 14c which detects a concentration of hydrogen within a distribution area 16 for hydrogen gas. If the concentration of hydrogen gas exceeds a first threshold value, this is regarded as a detection of feces, if confirmed by detection of a further gas determined by the further sensor 15. In this regard, the distribution area of the heavy organic compounds and the hydrogen sulfide is represented by means of reference numeral 17 in FIG. 5.

The threshold value of the concentration of hydrogen gas will be set to a concentration level of hydrogen gas which is expected to be present in a cubical 12a, 12b, 12c after a fecal insult occurred in the same cubicle 12a, 12b, 12c. The further gas sensor 15 may be arranged anywhere in the room, independently of the placement of the hydrogen sensors because the further gas, such as hydrogen sulfide, spreads widely and lingers due to its properties.

The location of feces may be registered by a receiving unit (not shown) in the same manner as descibed with reference to FIG. 4, and thereby visibly or audibly available to a user, e.g. a cleaner. One benefit of using the system in a public washroom is thus to provide reliable and up-to-date information regarding the location of fecal insult occurrences to the personnel of a public washroom.

The invention is not limited to the embodiments described above but can be varied within the scope of the appended claims.

The invention claimed is:

1. A method for determining a location of a fecal insult, comprising:
   detecting, by one of at least two first sensors, a concentration of hydrogen gas, which is at least one gas indicative of feces, each of the at least two first sensors at different ones of a first plurality of locations in a defined space;
   determining whether said concentration of hydrogen gas exceeds a predetermined first threshold value;
   detecting, by at least one second sensor, a concentration of at least one further gas component being indicative of feces, each of the at least one second sensor in said defined space, wherein said further gas component comprises at least one of an organic compound and hydrogen sulphide; and
   determining that a fecal insult has occurred in one of said first plurality of locations, which occurs where said concentration of hydrogen gas exceeds said first threshold value, provided that said concentration of said further gas component also exceeds a predetermined second threshold value, wherein there are fewer of said second sensors than said first sensors in said defined space.

2. The method according to claim 1, wherein the step of detecting the concentration of said further gas component occurs at an equal distance from each of said first plurality of locations where hydrogen gas is detected.

3. The method according to claim 1, wherein it is determined that a fecal insult has occurred in one of said first plurality of locations when said concentration of hydrogen gas has exceeded said first threshold value during a predetermined time period and said concentration of said further gas component has exceeded said second threshold value during a predetermined second time period.

4. The method according to claim 1, further comprises:
assigning a weight value for each of said concentration of hydrogen gas and said concentration of the further gas component before determining whether a fecal insult has occurred.

5. The method according to claim 1, wherein said first plurality of locations and location of said at least one second sensor in said defined space are at a predetermined distance from each other, which is longer than the radial distance that hydrogen gas may travel from its source of origin before a concentration of hydrogen is no longer detectable.

6. The method according to claim 1, further comprises:
registering said location of said fecal insult in a receiving unit.

7. A system for determining a location of a fecal insult, comprising:

a plurality of first gas sensors for detecting the concentration of at least one gas indicative of feces at a first plurality of locations in a defined space;

at least one further gas sensor for detecting the concentration of at least one further gas component being indicative of feces in said defined space at a second location, wherein said further gas component comprises at least one of an organic compound and hydrogen sulphide; and a receiver unit for determining whether said concentration of said gas exceeds a predetermined first threshold value, wherein said plurality of first gas sensors are configured for detecting said concentration of hydrogen gas at each of said first plurality of locations, wherein said receiver unit is configured to determine that a fecal insult has occurred in a location where said detected concentration of hydrogen gas exceeds said first threshold value, provided that the detected concentration of said further gas component also exceeds a predetermined second threshold value, and wherein there are fewer of said second sensors than said first sensors in said defined space.

8. The system according to claim 7, wherein the receiver unit comprises an indicator for providing visual or aural information as to the location where feces have been detected.

9. The system according to claim 7, further comprises a remote server unit connectable to said receiving unit and for storing information from said gas sensors.

10. The system according to claim 7, wherein said at least one further sensor unit is arranged an equal distance from each of said locations of said plurality of first sensors.

* * * * *